United States Patent [19]
Vertenstein et al.

[11] Patent Number: 5,167,629
[45] Date of Patent: Dec. 1, 1992

[54] VEIN LOCATOR

[76] Inventors: Mathieu J. Vertenstein, 3832 S. Rosemary Way, Denver, Colo. 80237; Mildred W. Lawson, 370 Adams St., Denver, Colo. 80206

[21] Appl. No.: 622,932

[22] Filed: Dec. 6, 1990

[51] Int. Cl.$^5$ .............................. A61M 5/00
[52] U.S. Cl. .................... 604/116; 604/115
[58] Field of Search ............ 604/115, 116, 117, 174, 604/175

[56] References Cited

U.S. PATENT DOCUMENTS

| | | | |
|---|---|---|---|
| 3,927,660 | 12/1975 | Tegtmeyer | 604/116 |
| 4,314,568 | 2/1982 | Loving | 604/116 |
| 4,425,119 | 1/1984 | Berglund | 604/175 |
| 4,527,569 | 7/1985 | Kolb | 604/116 |
| 4,667,679 | 5/1987 | Sahota | 604/116 |
| 4,886,501 | 12/1989 | Johnston | 604/175 |

OTHER PUBLICATIONS

Journal A.M.A. Jan. 4, 1930 (p. 26).

*Primary Examiner*—Paul J. Hirsch
*Attorney, Agent, or Firm*—Richard W. Hanes

[57] ABSTRACT

A vein locator for locating a vein of a patient for insertion of a venous access catheter. The locator comprises a sleeve partially encompassing the vein to be located, and a ring removably attached to the sleeve. The ring has protuberances around an opening wherein the protuberances can be felt through the skin of the patient to locate the vein. The opening surrounded by the protuberances defines the vein location for insertion of the catheter. The method of locating a vein and the method of inserting a venous access catheter is also contemplated by the invention.

7 Claims, 2 Drawing Sheets

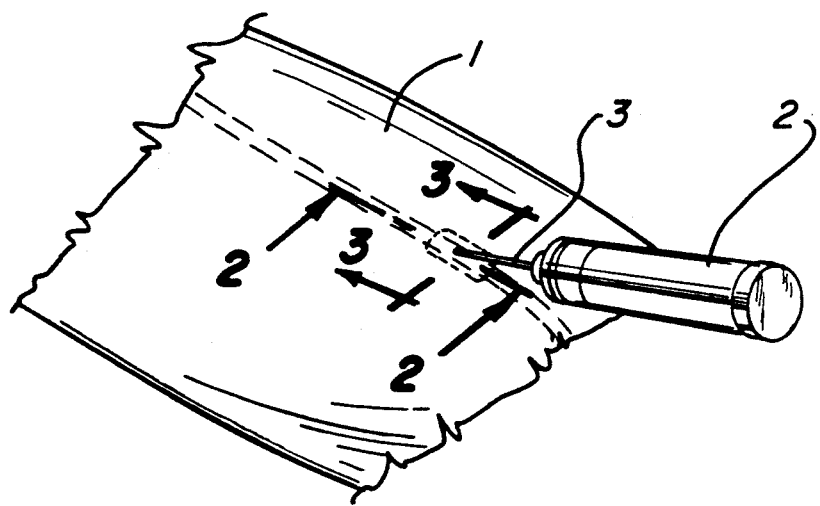
Fig_1
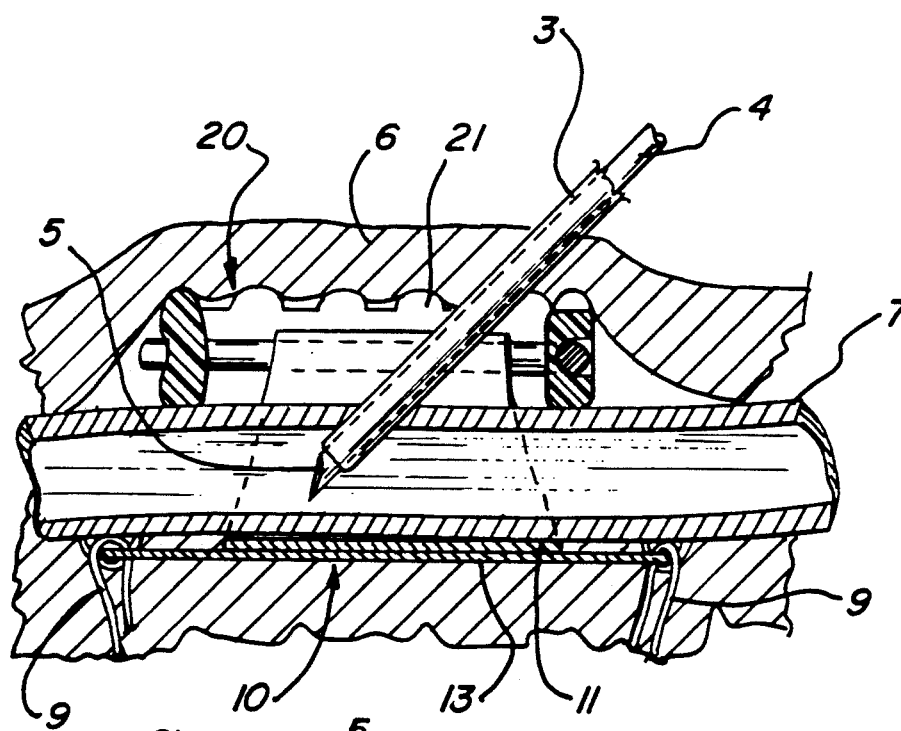
Fig_2
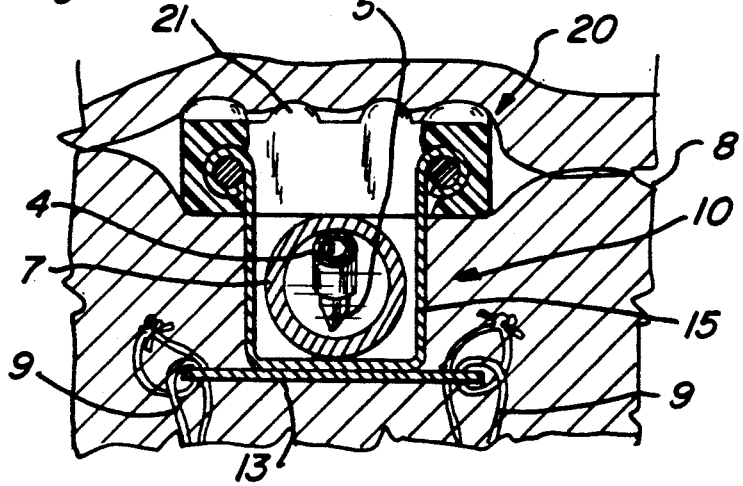
Fig_3

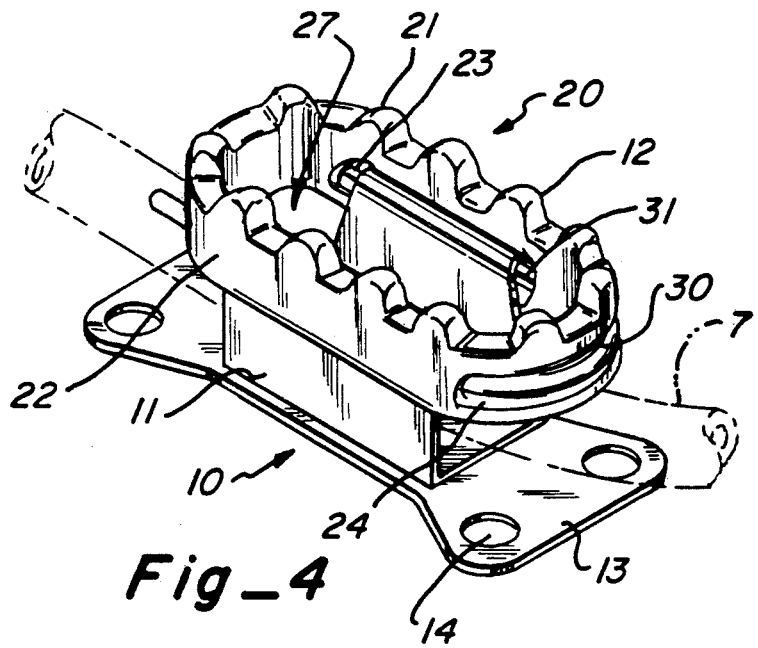
Fig_4
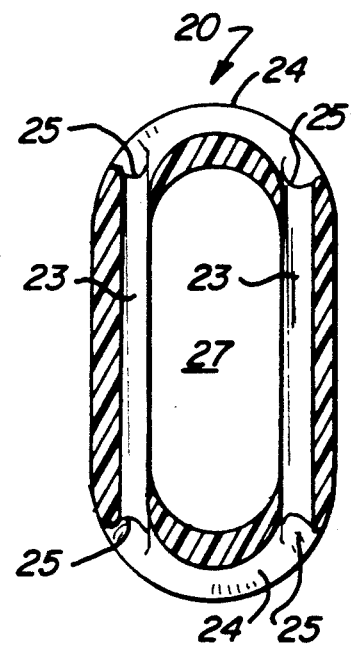
Fig_6
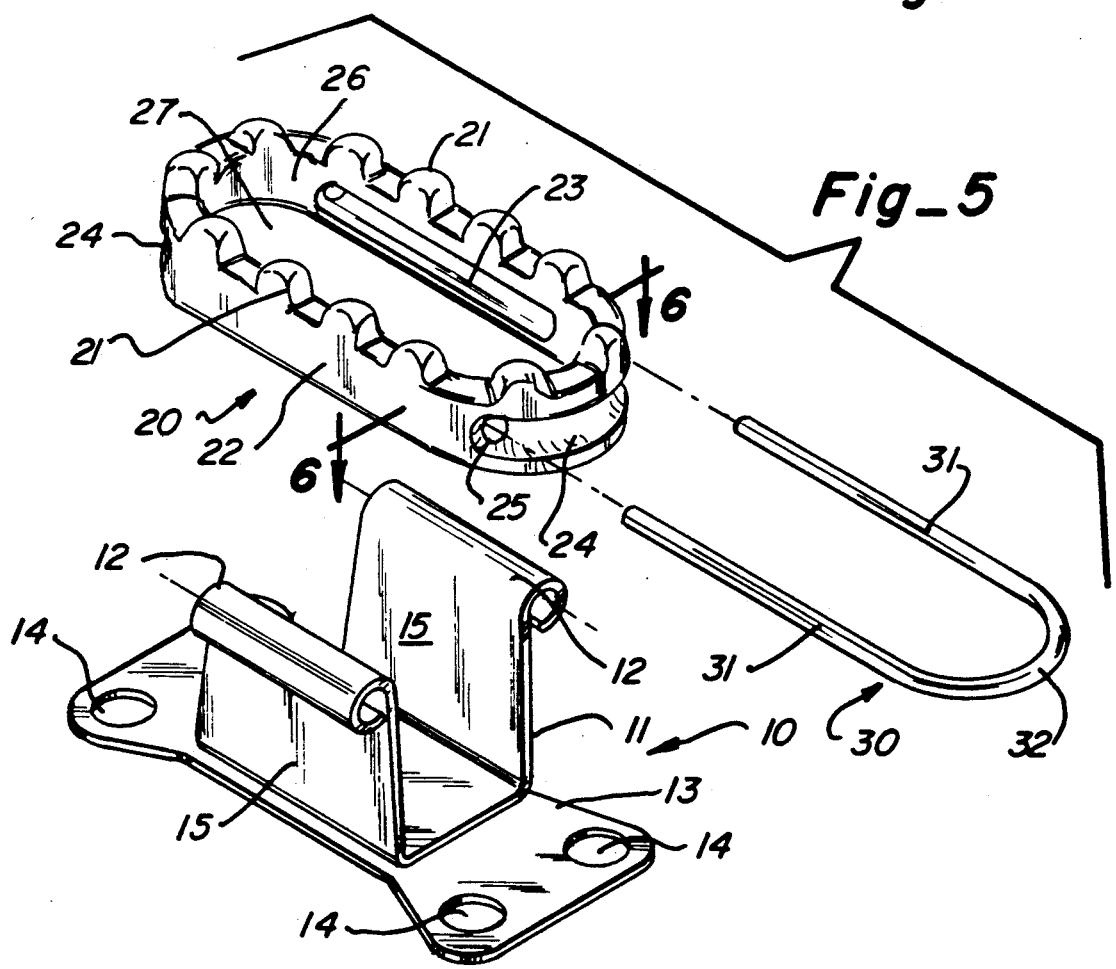
Fig_5

VEIN LOCATOR

BACKGROUND OF THE INVENTION

The instant invention relates to a vascular access guide or vein locator for patients requiring frequent and/or prolonged intravenous access for medical treatment. The method of locating and assuring proper access to a vein is also contemplated by the invention.

Many diseases require long-term continuous or intermittent intravenous therapy as a major part of their treatment including, but not limited to, such diseases as cancer, cystic fibrosis, renal disease, and major infections. During the last decade, many new intravenous access devices have been developed in order to administer the required medications into the patient's vein. However, problems associated with the insertion of these access devices and the trend to leave the devices indwelling in the vein for long periods of time (including times when they are not being used for drug and fluid administrations) can be dangerous to the patient.

One of the most frequently used methods for the insertion of an intravenous access device (catheter) is by percutaneous needle puncture directly into the vein with catheter insertion accomplished by an over the needle or through the needle technique. An over wire technique can also be used by inserting a guide wire through a needle, removing the needle, threading the access device or catheter into the vein using the wire as a guide and then removing the wire. In the past, it has been found that these methods could require several attempts to find an appropriate vein for catheter insertion. Every attempt to insert the catheter is associated with possible risks for major and possibly death-producing complications, such as pneumothorax, hemothorax, air embolism, vein or artery laceration and infections. It is obvious that by reducing the number of attempts for catheter insertion, one reduces accordingly the associated risks as mentioned. In addition to providing immediate access into the vein, due to its design with three-sided enclosure of the vein, the new vein locator would also reduce or eliminate some of the associated insertion risks such as pneumothorax induced by needle puncture of the lungs, and hemothorax induced by needle laceration of an artery or vein. Secondary to this would be the elimination or significant reduction of failed catheter insertions, with the implied risks of delaying critical and timely administration of intravenous medication to the patient. Moreover, the vein locator could significantly reduce the patient's pain and psychological trauma associated with difficult venous catheter insertion.

Following successful introduction of a percutaneously inserted venous catheter, the catheter customarily remains indwelling in the vein for the duration of the intravenous therapy, even if therapy is on an intermittent basis such as several days per month. The long-term indwelling catheter could also result in risks to the patient, including thrombus formation in or around the catheter, infection, phlebitis, air embolism, bleeding out of the catheter due to tubing or catheter breaks, and diminished quality of life due to the restraints of intensive maintenance care of the indwelling catheter.

Subcutaneously implanted vascular access portals with attached venous catheters are well known. However, their design involves a permanently attached, indwelling catheter, thus carrying the same inherent risks as mentioned for percutaneously inserted catheters. Another design is shown in U.S. Pat. No. 4,318,401 to Zimmerman. The portal of Zimmerman remains in the patient to receive catheters when required. A flange of the portal rests on or close to the outer skin surface of the patient. Thus, the portal would keep the skin of the patient available for the insertion of a catheter. Zimmerman's portal involves risks to the patient as: increased possibility of infection; permanently attached by sutures to the vein with difficult surgery involved for removal; and high accuracy required for fitting parts mechanically.

SUMMARY OF THE INVENTION

It is an object of the instant invention to provide a method for inserting an intravenous access catheter which would permit insertion of the catheter each time it is needed and allow removal of the catheter from the vein during periods of noninfusion.

It is a further object of the invention to provide a reliable vein locator to guide the safe insertion of a venous access catheter into the vein, and to then allow the catheter to be removed when fluids or medications are not being administered.

It is another object of the invention to provide a vein locator and guide for insertion of a catheter which allows the patient's skin to heal and close after catheter's removal to minimize the exposure of the patient's internal tissues and veins to air.

It is an additional object of the invention to provide a vein locator for allowing a care giver to accurately locate a patient's vein for any type of needle insertion.

The invention relates to a vein locator used as an aid in inserting a venous access catheter although it could also be used for locating a vein for other purposes, such as drawing blood. The locator includes a sleeve which partially encompasses the vein to be located. The sleeve in the preferred embodiment is sutured to subcutaneous tissues in a fixed location with respect to the vein. A ring is removably attached to the sleeve. A locking clip secures the ring onto the sleeve. The ring has protuberances around an opening wherein the edges of the protuberances can be felt by palpating the skin of the patient to locate the vein. The opening surrounded by the protuberances defines the vein location for insertion of the catheter. The vein locator is subcutaneous and therefore can remain under the patient's skin for subsequent use.

BRIEF DESCRIPTION OF THE DRAWINGS

FIG. 1 shows the insertion of a needle and catheter into a patient's vein with the elements under the skin being shown in dashed lines.

FIG. 2 is a typical cross-sectional view showing the skin and under skin structure taken along line 2—2 of FIG. 1.

FIG. 3 is a cross-sectional view similar to FIG. 2 taken along line 3—3 of FIG. 1.

FIG. 4 is an enlarged detail view of the vein locator showing the vein in dashed lines.

FIG. 5 is an exploded view of the vein locator device.

FIG. 6 is a cross-sectional view taken along line 6—6 of FIG. 5.

DESCRIPTION OF THE PREFERRED EMBODIMENT

The preferred embodiment is described in terms of locating a vein for insertion of a catheter to administer intravenous fluids. It is recognized that there are other reasons where it becomes necessary to locate a vein, for example, where blood is to be taken for periodic tests. Thus, the vein locator can be useful whenever it is necessary to locate a vein for repeated needle insertion.

In FIGS. 1 and 2, element 1 illustrates the area of the patient where it is desirable to provide intravenous therapy. A syringe 2 is utilized for insertion of needle 4 and catheter introducer 3. In FIG. 2, the needle point 5 pierces the patient's skin 6 and vein 7. Following insertion of items 3 and 4 in FIGS. 1 and 2, the needle 4 in FIG. 2 is removed from the catheter introducer 3. An intravenous catheter is threaded through the catheter introducer 3 and subsequently the catheter introducer is removed from the vein and eliminated according to manufacturer's guidelines. It is noted that other well known methods of inserting a catheter by means of a needle could also be used.

The location of the vein locator in the patient's body will now be described with reference to FIGS. 2 and 3. The sleeve 10 of the vein locator includes a U-shaped member 11 which surrounds the desired vein on two lateral sides as well as under it. The sleeve is sutured in place into tissues 8 by means of suturing thread 9. The ring 20 is attached to the top of the sleeve and includes protuberances 21 which lie just under the surface of the patient's skin 6. The protuberances identify the location of the vein as they can be felt when the surrounding skin is palpated. Once the protuberances have been detected, the venous access catheter can be inserted through the center 27 of the ring 20 in FIG. 5, as shown in FIG. 2.

The vein locator is positioned by a simple surgical procedure. The skin of the patient is initially incised for insertion of the sleeve 10. The sleeve comprises base plate 13, FIGS. 3, 4 and 6, and U-shaped portion 11. Items 13 and 11 can also be made in one piece. The baseplate 13 includes eyes 14 for suturing the baseplate 13 to surrounding tissues as described above. Although four eyes are illustrated, any number and position could be utilized to achieve the desired effect. The side walls of the U-shaped member end with curved tongues 12. The side walls 15 and curved tongues 12 are sized and biased to exert an outward pressure when ring 20 is attached. In the preferred embodiment, the sleeve is made of a biocompatible metal such as titanium, although other materials could be used.

Ring 20 is attached to sleeve 10. The ring 20 comprises an elongated oval shape around a hollow center or opening 27 although other shapes could also be used. The top portion of the ring is covered with a number of protuberances 21 at spaced intervals. The location and the shape of the protuberances can be selected so that they can be felt through the patient's skin. The location and shape of the protuberances should be such as to distinguish them from other organs, tumors, or body parts. The protuberances are subcutaneous as they lie under the surface of the patient's skin.

In the preferred embodiment, the ring 20, FIG. 4, is provided with two longitudinal channels 23. The channels 23 securely nest the tongues 12 of the sleeve 10. The channels can be manufactured by molding, drilling or other method. Their shape could be also approximated by successive, alternating teeth (not shown) or other geometry which could contribute to the cost reduction of the tooling and molding process. Coaxially and in continuation of the channels 23 are four apertures 25 which accept and nest the locking clip 30. When the locking clip 30 is inserted in the apertures 25, the tongues 12 become immovable and prevent the disassembly of the vein locator. The locking clip 30 is a U-shaped member having sides 31 and a curved central portion 32. The sides 31 pass through channels 23 and tongues 12 in the locked configuration of the locator. Cooperating with the apertures 25 are two recessed grooves 24 provided to receive and nest the central portion 32 of the locking clip 30. In other embodiments, these recessed grooves could be made as steps or eliminated altogether, this way exposing the portion 32 of the locking clip. As shown in FIG. 6, the channels 23 cooperate with the grooves 24 through apertures 25 to form a continuous chamber.

The preferred material for the ring is any biocompatible plastic with suitable mechanical characteristics although metals or other biocompatible materials could also be used.

The method of utilizing the vein locator will now be described with particular reference to the drawings.

To install the vein locator, a simple surgical procedure is required as noted above. An incision is made in the desired location and the patient's skin is parted to insert the components of the locator. It is noted that the vein locator will be most practical when extensive intravenous access is likely to occur. Thus, the vein locator could probably be initially inserted during an operation required by the patient's primary medical treatment.

During the surgical procedure, the sleeve 10 is initially fitted around the vein to be located. The sleeve 10 is arranged with side walls 15 around the vein 7 and with base 13 underlying the vein 7. The sleeve 10 is then sutured in place to the tissues by means of eyes 14 and thread 9. Other well known methods, such as stapling, could be used to attach the sleeve 10 to the underlying tissues. The configuration of the sleeve's walls 15 aid in protecting any surrounding vital organs from injury during placement of an intravenous access catheter. The use of the side walls 15 also prevents the vein 7 from slipping out of the vein locator.

After the sleeve 10 is secure, ring 20 is attached to the sleeve. The surgeon or installer squeezes the side walls 15 against their bias so that they can fit through opening 27 in the ring 20. When the walls 15 are released, the tongue portions 12 of the walls 15 will nest in channels 23 of the ring 20. The nesting tongues 12 exert a substantial sideways pressure on the channels 23 to secure the ring in place. Locking pin 30 is then inserted through one pair of apertures 25. Note recessed grooves 24 and apertures 25 are provided on opposite sides of the ring so that the locking pin 30 can be inserted from either side depending on which is preferable considering the surrounding body organs and tissues. In the locked configuration, the arm portions 31 of the clip 30 extend through the channels 23 and tongues 12. Once locking clip 30 is secure, accidental disassembly is difficult.

After the surgical procedure, the overlying skin is allowed to heal, thus the vein locator does not have a percutaneous or through the skin component. Thus, after each treatment with a venous access catheter, the percutaneous catheter can be removed and the skin again allowed to heal.

The use of the catheter will now be explained with reference to FIGS. 1, 2 and 3. Initially, skin 6 is palpated in order to detect the vein locator. The protuberances 21, felt through the skin, help define opening 27 in the ring. The catheter can then be inserted through opening 27 of the vein locator by any well known means, such as insertion needle 4 and the catheter introducer 3. Note that the shape of ring 20 allows an angled needle entry into the vein. After the removal of needle 4 and the catheter introducer 3 and the administration of the medication through the catheter, the catheter itself can be removed. Thus, the skin can again heal over the vein locator. Since the catheter does not remain in the patient's body, maintenance care, including dressings and daily flushing of the catheter, can be eliminated.

Should it become necessary to remove the vein locator, another simple surgical procedure can be performed. Once the skin is opened and the vein locator exposed, the surgeon can remove locking pin 30 and squeeze sides 15 to remove the tongues 12 from the nesting channels 23. Ring 20 can then be easily lifted off sleeve 10. The surgeon then clips sutures holding sleeve 10 from the underlying tissues for removal.

The method of assembly between the sleeve 10 and ring 20, as well as between sleeve 10 and base 13, is shown as a preferred embodiment, considering cost and practicality during its surgical installation. However, other methods of assembly could be used, such as fastening with screws, wires, rivets, clips, cement, elastomers of any shape, welding, etc. as long as none of the vein locator's components protrude into the vein or through the skin.

It is important that all edges of the vein locator's components are well rounded and the surfaces as smooth as compatible with economical manufacturing practice. This prevents the vein locator from piercing or otherwise damaging other body organs. Also, the vein locator can be designed in several sizes compatible with the sizes of various veins and with the patient's body.

We claim:

1. A device for locating a blood vessel by palpation, to be subcutaneously located and positioned to surround a limited length of the blood vessel to be acquired comprising, body means having a bottom and side walls and open ends and an open top to confine therein a length of the blood vessel, target forming ring means disposed around the open top portion of the body, said ring means having a ribbed upper surface which lies under the skin and which may be palpated to locate the position on the skin which is directly above the blood vessel.

2. The blood vessel locating device of claim 1 wherein said target forming ring means is removably attached to said body means.

3. A vein locator for locating the vein of a patient, comprising means for confining the vein to be located, ring means attached to said confining means, said ring means having protuberant edges on a surface thereof;

wherein said means for confining comprises sleeve means for at least partially surrounding the vein to be located;

wherein said ring means is removably attached to said sleeve means and wherein said sleeve means comprises a U-shaped member having first and second upstanding arms and first and second tongue means attached respectively to said upstanding arms, said ring means comprising first and second channels for respectively receiving said first and second tongue means, so that when said ring means is attached to said sleeve means, said first tongue means rests in said first channel and said second tongue means rests in said second channel, said upstanding arms biasing said first and second tongue means to nest said first and second tongue means in said respective channels.

4. The vein locator of claim 3 comprising a locking means having a locked configuration for locking said ring means to said sleeve means and wherein said locking means comprises first and second arm portions and a central portion connecting said first and second arm portions, and wherein in said locked configuration, said first arm portion extends through said first tongue means and said first channel and said second arm portion extends through said second tongue means and said second channel.

5. The vein locator of claim 4 wherein said ring means comprises a groove for receiving said central portion of said locking means in said locked configuration.

6. The method of locating a blood vessel in a patient comprising;

subcutaneously placing a non vessel invasive locator apparatus, having a protuberant skin facing target area, so as to surround, just below the said target area, a limited length of the blood vessel to be acquired, and palpating the surface of the patient's skin to feel the protuberant target area beneath the skin and thereby to locate the position for inserting a needle into the blood vessel.

7. The method of claim 6 wherein said step of subcutaneously placing a blood vessel locator comprises, attaching a sleeve under the skin of the patient so that said sleeve surrounds a length of the vessel to be acquired, attaching a target ring to said sleeve so that said ring lies over the vessel and under the skin of the patient and said edges are carried by said target ring.

* * * * *